US00PP37716P2

(12) United States Plant Patent
Wain

(10) Patent No.: US PP37,716 P2
(45) Date of Patent: Sep. 29, 2026

(54) ***CHRYSANTHEMUM* PLANT NAMED 'Dochryjobro'**

(50) Latin Name: ***Chrysanthemum* X *morifolium***
Varietal Denomination: Dochryjobro

(71) Applicant: DUMMEN GROUP B.V., De Lier (NL)

(72) Inventor: Peter Wain, Locks Heath (GB)

(73) Assignee: DÜMMEN GROUP B.V., De Lier (NL)

( * ) Notice: Subject to any disclaimer, the term of this patent is extended or adjusted under 35 U.S.C. 154(b) by 0 days.

(21) Appl. No.: 19/538,680

(22) Filed: Feb. 12, 2026

(51) Int. Cl.
*A01H 5/02* (2018.01)
*A01H 6/14* (2018.01)

(52) U.S. Cl.
USPC ..... Plt./290
CPC ..... *A01H 6/1424* (2018.05)

(58) Field of Classification Search
USPC ..... Plt./290, 296
CPC ..... A01H 5/0255
See application file for complete search history.

*Primary Examiner* — Kent L Bell
(74) *Attorney, Agent, or Firm* — C. Anne Whealy

(57) ABSTRACT

A new and distinct cultivar of *Chrysanthemum* plant named 'Dochryjobro', characterized by its compact, upright to outwardly spreading and uniformly and mounded plant habit; moderately vigorous growth habit; freely branching habit; dense and full plant form; early to mid-season and freely flowering habit; decorative-type inflorescences with bronze-colored ray florets; and good garden performance.

1 Drawing Sheet

Botanical designation: *Chrysanthemum* X *morifolium*.
Cultivar denomination: 'DOCHRYJOBRO'.

BACKGROUND OF THE INVENTION

The present invention relates to a new and distinct *Chrysanthemum* plant, botanically known as *Chrysanthemum* X *morifolium*, commercially grown as a garden *Chrysanthemum* plant and hereinafter referred to by the name 'Dochryjobro'.

The new *Chrysanthemum* plant is a product of a planned breeding program conducted by the Inventor in Fareham, Hampshire, United Kingdom. The objective of the breeding program is to create new uniform and early-flowering garden *Chrysanthemum* plants with numerous attractive inflorescences.

The new *Chrysanthemum* plant originated from a cross-pollination made in August, 2018 by the Inventor in Fareham, Hampshire, United Kingdom of a proprietary selection of *Chrysanthemum* X *morifolium* identified as code number 805373, not patented, as the female, or seed, parent with a proprietary selection of *Chrysanthemum* X *morifolium* identified as code number 804340, not patented, as the male, or pollen, parent. The new *Chrysanthemum* plant was discovered and selected by the Inventor as a single flowering plant from within the progeny of the stated cross-pollination in a controlled greenhouse environment in Fareham, Hampshire, United Kingdom in April, 2019.

Asexual reproduction of the new *Chrysanthemum* plant by terminal vegetative cuttings was first conducted in Fareham, Hampshire, United Kingdom in December, 2019. Asexual reproduction by terminal vegetative cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Dochryjobro'. These characteristics in combination distinguish 'Dochryjobro' as a new and distinct garden *Chrysanthemum* plant:

1. Compact, upright to outwardly spreading and uniformly and mounded plant habit.
2. Moderately vigorous growth habit.
3. Freely branching habit; dense and full plant form.
4. Early to mid-season and freely flowering habit.
5. Decorative-type inflorescences with bronze-colored ray florets.
6. Good garden performance.

Plants of the new *Chrysanthemum* can be compared to plants of the female parent selection. Plants of the new *Chrysanthemum* differ primarily from plants of the female parent selection in the following characteristics:

1. Plants of the new *Chrysanthemum* are more compact than plants of the female parent selection.
2. Plants of the new *Chrysanthemum* flower slightly later than plants of the female parent selection.
3. Ray florets of plants of the new *Chrysanthemum* are bronze in color whereas ray florets of plants of the female parent selection are pink in color.

Plants of the new *Chrysanthemum* can be compared to plants of the male parent selection. Plants of the new *Chrysanthemum* differ primarily from plants of the male parent selection in the following characteristics:

1. Plants of the new *Chrysanthemum* flower slightly later than plants of the male parent selection.

2. Ray florets of plants of the new *Chrysanthemum* are bronze in color whereas ray florets of plants of the male parent selection are yellow in color.

Plants of the new *Chrysanthemum* can also be compared to plants of *Chrysanthemum* X *morifolium* 'Cruise Yellow', not patented. In side-by-side comparisons, plants of the new *Chrysanthemum* differ primarily from plants of 'Cruise Yellow' in the following characteristics:

1. Plants of the new *Chrysanthemum* are more compact than plants of 'Cruise Yellow'.
2. Plants of the new *Chrysanthemum* flower slightly later than plants of 'Cruise Yellow'.
3. Plants of the new *Chrysanthemum* have bronze-colored ray florets whereas plants of 'Cruise Yellow' have yellow- colored ray florets.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant. The photograph is a side perspective view of a typical flowering plant of 'Dochryjobro' grown in a container.

DETAILED BOTANICAL DESCRIPTION

The aforementioned photograph and following observations and measurements describe plants grown during the autumn and winter in 19-cm containers in a glass-covered greenhouse in De Kwakel, The Netherlands and under cultural practices typical of commercial garden *Chrysanthemum* production. During the production of the plants, day temperatures ranged from 21 °C to 25 °C, night temperatures ranged from 17 °C to 19 °C and light levels averaged 7,000 lux. Plants were propagated and grown under long day/short night conditions for five weeks and then grown under short day/long night conditions to induce inflorescence initiation and development. Plants were 16 weeks old when the photograph and detailed description were taken. In the following description, color references are made to The Royal Horticultural Society Colour Chart, Fifth Edition, except where general terms of ordinary dictionary significance are used.

Botanical classification: *Chrysanthemum* X *morifolium* 'Dochryjobro'.

Parentage:

*Female, or seed, parent*.—Proprietary selection of *Chrysanthemum* X *morifolium* identified as code number 805373, not patented.

*Male, or pollen, parent*.—Proprietary selection of *Chrysanthemum* X *morifolium* identified as code number 804340, not patented.

Propagation:

*Type*.—Terminal vegetative cuttings.

*Time to initiate roots, summer*.—About ten days at temperatures about 21 °C.

*Time to initiate roots, winter*.—About twelve days at temperatures about 21 °C.

*Time to produce a rooted young plant, summer*.—About three weeks at temperatures about 21 °C.

*Time to produce a rooted young plant, winter*.—About four weeks at temperatures about 21 °C.

*Root description*.—Medium in thickness, fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous decorative-type garden *Chrysanthemum*; compact with stems upright to outwardly spreading giving a uniformly mounded appearance to the plant; numerous lateral branches and relatively short internodes, dense and full plant form; hemispherical in overall plant shape; moderately vigorous growth habit and medium growth rate.

*Plant height*.—About 13 cm.

*Plant width*.—About 21 cm.

*Branching habit*.—Freely branching habit; about nine lateral branches develop per plant.

*Lateral branches*.—Length: About 11 cm. Diameter: About 4 mm. Internode length: About 1.5 cm. Aspect: Upright to about 65° to 70°. Texture and luster: Pubescent; matte. Color: Close to 137D; at the internodes, close to 137C; with development, color becoming closer to 137B.

Leaf description:

*Arrangement*.—Alternate, simple.

*Length*.—About 4.5 cm.

*Width*.—About 2.9 cm.

*Shape*.—Palmately-lobed; roughly ovate in overall outline with three to five lobes.

*Apex*.—Acute.

*Base*.—Attenuate.

*Margin*.—Palmately lobed and slightly dentate; sinuses between lateral lobes divergent and medium in depth.

*Texture and luster, upper and lower surfaces*.—Sparsely pubescent; matte.

*Venation pattern*.—Pinnate.

*Color*.—Developing and fully expanded leaves, upper surface: Close to 137A; venation, close to 147D. Developing and fully expanded leaves, lower surface: Close to 138B; venation, close to 147D.

*Petioles*.—Length: About 1 cm. Diameter: About 3 mm. Texture and luster, upper and lower surfaces: Sparsely pubescent; matte. Color, upper and lower surfaces: Close to 147D.

Inflorescence description:

*Form and flowering habit*.—Decorative-type inflorescence form with ligulate-shaped ray florets; inflorescences borne on terminals above and beyond the foliar plane; disc and ray florets arranged acropetally on a capitulum; freely flowering habit with about 13 inflorescences developing per lateral branch and about 100 inflorescences developing per plant; inflorescences face mostly upright to somewhat outwardly.

*Fragrance*.—Mildly fragrant; pungent, herbaceous.

*Flowering response*.—Early to mid-season flowering habit, plants begin flowering about 80 days after start of photoinductive treatments; under natural season flowering conditions, plants of the new *Chrysanthemum* flower continuously from early September to late September in De Kwakel, The Netherlands.

*Inflorescence longevity*.—Inflorescences maintain good color and substance for about three to five weeks on the plant; inflorescences persistent.

*Inflorescence buds*.—Height: About 8 mm. Diameter: About 6 mm. Shape: Oblate. Texture and luster: Smooth, glabrous; slightly glossy. Color: Close to 180A and 181B.

*Inflorescence diameter*.—About 3.6 cm.

*Inflorescence height*.—About 1.8 cm.

*Disc diameter*.—To date, disc floret development has not been observed on plants of the new *Chrysanthemum*.

*Receptacles*.—Height: About 3 mm. Diameter: About 3 mm. Shape: Conical. Color: Close to 145B.

*Ray florets*.—Number of ray florets per inflorescence: About 133 arranged in about nine whorls. Orientation: Initially upright, then about 80° from vertical with development. Length: About 2 cm. Width: About 6 mm. Shape: Ligulate. Apex: Acute. Base: Fused into a short tube. Margin: Entire. Texture and luster, upper and lower surfaces: Smooth, glabrous; matte. Color: When opening, upper surface: Close to 173B and 180B. When opening, lower surface: Close to 173D. Fully opened, upper surface: Close to 173A and 181A; venation, similar to lamina; color becoming closer to 173A with subsequent development. Fully opened, lower surface: Close to 182B; venation, similar to lamina; color becoming closer to 173D with subsequent development.

*Phyllaries*.—Number of phyllaries per inflorescence: About 22 arranged in about three whorls. Length: About 6 mm. Width: About 3 mm. Shape: Lanceolate. Apex: Obtuse, rounded. Base: Obtuse, rounded. Margin: Entire. Texture and luster, upper surface: Smooth, glabrous; waxy; matte. Texture and luster, lower surface: Pubescent, waxy; matte. Color, upper surface: Close to 137C. Color, lower surface: Close to 137B.

*Peduncles*.—Length, uppermost peduncle: About 2.7 cm. Diameter, uppermost peduncle: About 2 mm. Aspect: Upright to about 20° from lateral branch axis. Texture and luster: Pubescent; matte. Color: Close to 138B.

*Reproductive organs*.—Androecium: None observed. Gynoecium: Pistil length: About 4 mm. Stigma shape: Bi-parted. Stigma color: Close to 154A. Style length: About 3 mm. Style color: Close to 142C. Ovary color: Close to 157D.

*Seeds and fruits*.—To date, seed and fruit production has not been observed on plants of the new *Chrysanthemum*.

Pathogen & pest resistance: Plants of the new *Chrysanthemum* have been observed to be resistant to White Rust (*Puccinia horiana*) and *Fusarium* Wilt (*Fusarium oxysporum*). To date, resistance to pests and other pathogens common to *Chrysanthemum* plants has not been observed on plants of the new *Chrysanthemum*.

Garden performance: Plants of the new *Chrysanthemum* have demonstrated good garden performance and to tolerate temperatures from about 0 °C to about 35 °C.

It is claimed:

1. A new and distinct *Chrysanthemum* plant named 'Dochryjobro' as herein illustrated and described.

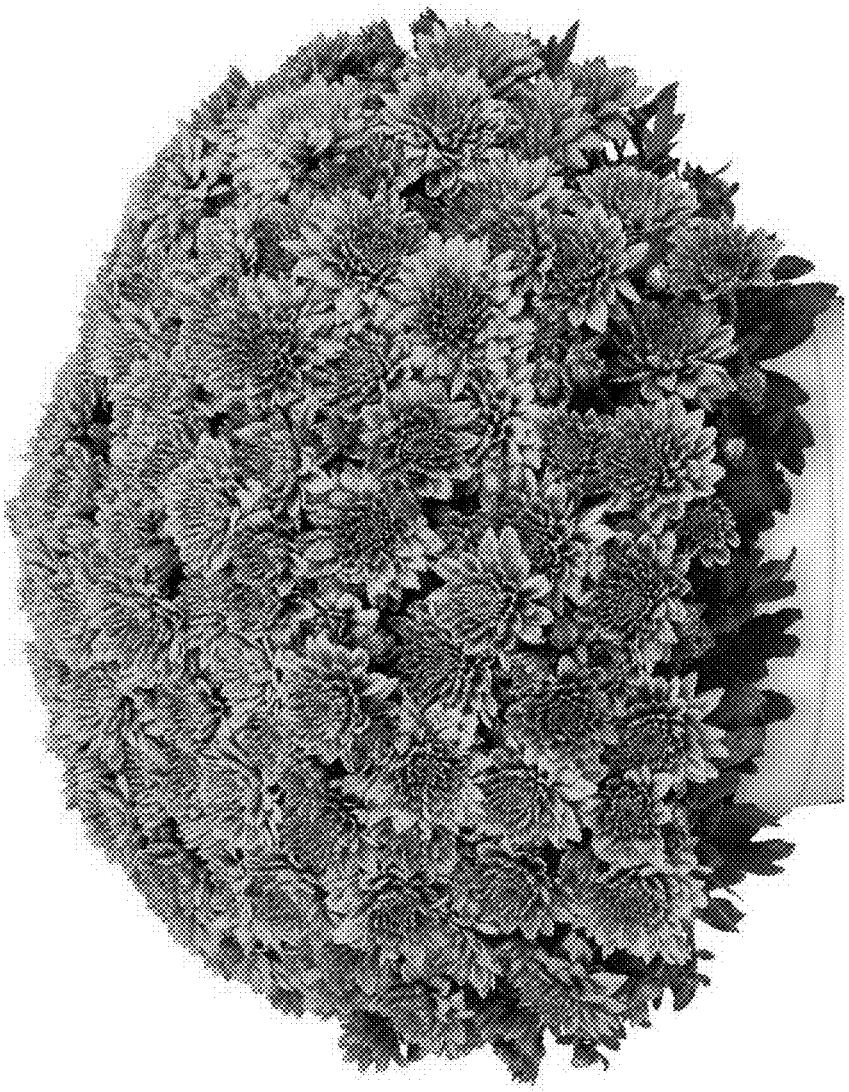

* * * * *